United States Patent [19]

Russell et al.

[11] 4,049,007

[45] Sept. 20, 1977

[54] PERMANENT WAVING OF HUMAN HAIR BY MEANS OF CROSSLINKING URETHANE AND/OR HYDROXAMATE DERIVED FROM REACTIVE ACRYLIC RESINS AND ADIPODINITRILE CARBONATE

[75] Inventors: Donald H. Russell, Cherry Hill, N.J.; Charles J. Kremer, Brookhaven, Pa.

[73] Assignee: Atlantic Richfield Company, Los Angeles, Calif.

[21] Appl. No.: 672,578

[22] Filed: Apr. 1, 1976

Related U.S. Application Data

[63] Continuation-in-part of Ser. No. 579,765, May 22, 1975, abandoned, which is a continuation of Ser. No. 400,099, Sept. 24, 1973, abandoned, which is a continuation-in-part of Ser. No. 307,281, Nov. 16, 1972, abandoned.

[51] Int. Cl.² ............................................. A45D 7/00
[52] U.S. Cl. ......................................... 132/7; 424/71
[58] Field of Search ............................... 132/7; 424/71

[56] References Cited

U.S. PATENT DOCUMENTS

| 3,577,518 | 5/1971 | Shepherd | 424/71 |
| 3,741,723 | 6/1973 | Kalopissis | 424/71 |
| 3,954,960 | 5/1976 | Valan | 424/71 |

*Primary Examiner* — G.E. McNeill
*Attorney, Agent, or Firm* — Coleman R. Reap

[57] ABSTRACT

Compounds suitable for use in waving human hair comprised of a film-forming resin containing pendant hydroxyl, amine, and/or thiol groups; a cyclic nitrile carbonate of the formula

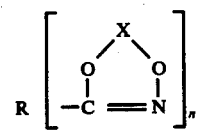

wherein R is an organic radical having 1 to about 200,000 carbon atoms, X is

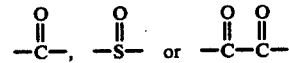

and n is at least 2; and a flexibilizing adhesion promoter; and optionally a catalyst. The composition is preferably dissolved in a non-aqueous solvent. Hair is waved by contacting the hair with the composition and drying it at room or elevated temperatures.

34 Claims, No Drawings

PERMANENT WAVING OF HUMAN HAIR BY MEANS OF CROSSLINKING URETHANE AND/OR HYDROXAMATE DERIVED FROM REACTIVE ACRYLIC RESINS AND ADIPODINITRILE CARBONATE

BACKGROUND OF THE INVENTION

This application is a continuation-in-part of copending application Ser. No. 579,765 filed May 22, 1975 now abandoned, which is a Streamline continuation of application Ser. No. 400,099 filed Sept. 24, 1973, now abandoned, which is a continuation-in-part of application Ser. No. 307,281 filed Nov. 16, 1972, now abandoned.

This invention relates to the waving of hair and more particularly to an improved process for the permanent waving of human hair, and new compositions used in the process.

One of the oldest practices in the field of cosemtology is the artificial waving of hair. Women have applied various treatments to their hair to improve the degree of curl in the hair since the early days of the ancient Egyptian civilization. It was not, however, until the present century that long-lasting hair waving, more commonly known as permanent waving, was developed. The waving of hair in early times was accomplished by physical methods, that is by setting the hair and applying a composition to hold the set without chemically altering the nature of the hair. Modern permanent hair waving procedures include the use of chemical treatments which involve the temporary alternation of the chemistry of the hair.

The most common permanent waving process practiced today consists essentially of three steps; softening, setting, and hardening the hair. In the softening step, a solution containing a reducing agent is applied to the hair. The reducing agent attacks the disulfide linkages of the cystine molecules, which largely make up the keratin fibers of the hair, causing them to split. The scission of the disulfide linkages causes the hair to lose its stiffness. After a sufficient number of disulfide linkages are broken, the hair becomes soft enough to set, at which point it is tightly wound on curlers to impart to the hair the desired shape. The hair is next treated, while it is still mounted on the curlers, with a hardening or neutralizing solution. The hardening solution contains an oxidizing agent which causes many of the disulfide linkages to be reformed, resulting in the reestablishment of the hard nature of the keratin fibers. Thus modified, the hair will retain its curl for several months, provided that the permanent wave was applied properly and took well.

There are a number of disadvantages which attend the permanent waving of hair by the above described procedure. In the first place, the entire process is extremely time consuming and usually requires the person obtaining the permanent wave to sit in the beauty parlour for many hours, generally on the order of 4 to 6 hours. Secondly, the success of the permanent wave depends on the expertise of the hair dresser in determining the amount of softener and hardner to use, the length of time that ech step is carried out, the temperature of the drying step, etc. The selection process of the procedure is further complicated by the fact that the nature of the hair being treated varies considerably from one client to the next. Another major disadvantage of the above-described permanent waving process is the fact that the use of the necessary harsh reducing and oxidizing agents often leads to a weakening of the hair and splitting of the ends of the hair. In some cases the reaction to the use of these chemicals has been so severe that portions of the hair have fallen out. An additional disadvantage of the above hair waving procedure is that it must generally be practiced in a beauty parlour, and due to the length of time and the degree of skill required to do a satisfactory job, professional permanent waving is very expensive. Still another major disadvantage of the above-described permanent waving practice is the fact that the chemical reactions involved cause the release of volatile sulfur compounds, particularly sulfur dioxide which produces an obnoxious odor.

The foregoing and other disadvantages of conventional permanent waving practices have led to the development of home permanent waving kits which enable women to give themselves a permanent wave. Home waving processes, unfortunately, usually require the same steps as the abovedescribed process and, accordingly, have the same disadvantages. The only principal advantage of home permanents over those performed in a beauty parlour is that the home permanent waving kits usually cost only a few dollars, but this is greatly offset by the many disadvantages of home permanent waving, particularly when the person applying the wave is relatively inexperienced. If any of the steps (as many as 16 separate steps) are omitted, or improperly carried out, the permanent wave will not take or will be considerably inferior to that obtained in a beauty parlour by a professional hairdresser. In view of these disadvantages, home permanent kits have not become very popular.

Other attempts to impart curl to hair without the above complicated and costly procedures have led to the development and wide-spread use of compositions which, when applied to the hair, impart a physical set. Such compositions usually contain lacquers or polymeric substances which dry to hard resinous substances. These hair setting procedures are carried out by applying the setting solution to the hair and mounting the wet hair in curlers. After the setting solution has dried, the curlers are removed and the hair is combed. The hair, which now contains a resinous film, retains a portion of the curl imparted by the hair curlers. The principal disadvantage of this method of setting hair is that the set is not very tight, and in wet or humid weather the hair rapidly loses the set, due to the fact that the hair setting solutions are, to a great degree, water-soluble.

It is evident that the above methods for curling hair leave a lot to be desired and improved waving procedures and compositions are constantly sought.

SUMMARY OF THE INVENTION

A new permanent waving composition has now been developed which makes it possible to impart a long-lasting permanent wave to human hair without suffering the aforementioned disadvantages. Accordingly, it is an object of the present invention to present a new permanent wave composition. It is another object of the invention to present compositions and solutions which will impart a long-lasting curl to human hair without adversely affecting the chemical nature of the hair. It is a third object of the invention to present a process for permanent waving hair without the use of harsh chemical reducing and oxidizing agents. It is another object of the invention to provide an inexpensive and efficient, simplified method of permanently waving hair. It is a further object of the invention to present a method of permanently waving hair which can be accomplished in a relatively short period of time. It is another object of the invention to present a method of permanently waving hair to produce a curl which has little or no sensitivity to moisture. These and other objects of the present invention will become apparent as the description proceeds.

In accordance with the invention, compositions suitable for use in the permanent waving of human air are presented, which compositions are comprised of a film-forming organic resin, a cyclic nitrile compound, and a flexibilizing adhesion promoter. A catalyst effective for speeding up the reaction between the film-forming polymer and the cyclic carbonate is optional. The compositions of this invention are preferably dissolved or dispersed in a non-aqueous organic solvent.

The film-forming resin useful in the present invention are those organic polymers having pendant groups containing a reactive hydrogen. The preferred pendant groups are hydroxyls, primary amines, secondary amines, thiols, and mixtures of these. The preferred resins are film-forming acrylic polymers having pendant groups which contain reactive hydrogens. The cyclic nitrile compound has the structure

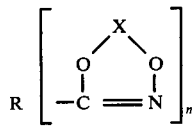

wherein R is an organic radical having from 1 to about 200,000 preferably 1 to 10 carbon atoms, and is free of nucleophilic groups, X is

and $n$ is 2 to 4. The flexibilizing adhesion promoter may be any of the known plasticizer agents generally used with polymers which are free of atoms or chemical groups which would interfere with the hair waving activity of the invention, quaternary vinyl pyrrolidone polymers, epichlorohydrinmodified water-soluble polyamides containing, prior to modification with epichlorohydrin, secondary amine groups, or mixtures of any of these.

The catalysts optionally used in the invention are any of the catalysts useful in catalyzing the reaction between cyclic nitrile compounds and functional hydrogencontaining groups. The preferred catalysts are the basic catalysts, for example, tertiary amines. The organic solvent may be any organic liquid in which the waving composition is soluble or dispersable and which does not interfere with the activity of the waving composition. The preferred solvents are methylene chloride, fluorochloro alkanes containing up to 3 carbon atoms, and alkanols containing up to 3 carbon atoms.

The process of the invention comprises the steps of treating the hair with the above compositions and drying the hair at room or elevated temperatures. The drying may be conducted at a temperature sufficiently high to effect rapid curing of the polymer or the polymer may be permitted to cure slowly at room temperature, as overnight.

DESCRIPTION

The film-forming resins which are useful in the present invention are those organic polymers which contain pendant groups having reactive hydrogen as determined by the Zerewitinoff test and which are free of elements or chemical groups which interfere with the ability of the composition to perform as a hair permanent waving agent. Groups which contain reactive hydrogen, as determined by the Zerewitinoff test, are those which, when contacted with a Grignard solution of methyl iodide, will effect the liberation of methane by the decomposition of the Grignard reagent. Groups containing a reactive hydrogen in accordance with this definition include hydroxyl, primary and secondary amine, and thiols. The reactive hydrogencontaining group may be located either in the chain of the polymer or pendant to it or the polymer may contain both in-chain and pendant reactive hydrogen-containing groups. In addition, suitable polymers may contain a mixture of hydroxyl, amine or thiol groups at positions located in-chain, pendant or combinations of the two.

Included in this class of polymers are hydroxyl, amine-, and thiol-containing vinyl polymers and copolymers of vinyl acetate in which about 10 to 50% of the acetate groups are hydrolyzed; reactive hydrogen-containing modified acrylate and methacrylate polymers wherein the esterifying moiety is a reactive hydrogen-substituted saturated hydrocarbon radical having 1 to 20, preferably 1 to 6 carbon atoms, such as poly(2-hydroxyethyl acrylate), poly(2-mercaptobutyl methacrylate), poly(6-aminohexyl acrylate), etc. and reactive hydrogen-containing ketimino substituted acrylate and methacrylate monomers having the structural formula:

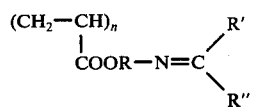

wherein R is a saturated hydrocarbon radical having 1 to 20 and preferably 1 to 6 carbon atoms, R' and R" are the same or different alkyl or aryl groups containing 1 to 8 and preferably 3 to 6 carbon atoms. R' and R" are blocking groups which are moisture and/or heat removable. A representative ketimino polymer is poly(di-n-butyl ketimino ethyl acrylate).

The above monomers may be copolymerized with other vinyl monomers such as aliphatic compounds, such as vinyl chloride, vinyl acetate, acrylic acid, acrylonitrile, acrylates and methacrylates, etc.; and aromatic compounds, such as styrene, vinyl toluene and chloro styrene; and heterocyclic compounds such as vinyl pyrrolidone and vinyl pyridine.

Typical copolymers include n-butyl acrylate di-n-butyl ketimino ethyl acrylate copolymer, styrene-2-hydroxyethyl methacrylate copolymer, vinyl chloride-ethylphenyl ketimino butyl methacrylate copolymer, vinyl pyrrolidone-vinyl acetate-2-mercaptoethyl acrylate terpolymer, acrylonitrile-3-aminopropyl methacrylate copolymer, etc.

Other suitable reactive hydrogen-containing polymers are the hydroxyl, amine and thiol-containing condensation polymers and copolymers such as polyurethanes, polyureas, polyesters, polyethers, and alkyd resins made from polyols, polyamines and polythiols having more than two reactive hydrogen groups per molecule. The preferred group of polymers for use in the composition are the hydroxyl, amine and/or thiol-containing acrylic and methacrylic resins, including polymers and copolymers, since these resins provide a clear, tough polymeric film which will not yellow with the passage of time. Since one of the functions of the resin in the invention is to form a film over the surface of the individual strands of hair, it is important that the resin being employed have film-forming properties. The term film-forming, as used in this discussion, means the ability to form a continuous coating when applied to a surface. In an alternate embodiment, a resin-forming precursor may be substituted for all or a portion of the film-forming resin. Such precursors are those which will react rapidly under the conditions of use of the hair waving composition to produce a continuous film resin. Exemplary of such precursors are compounds having the formula:

$$RX_n$$

wherein R represents an organic radical, X is OH, NH$_2$, NH or SH and $n$ is greater than 2. Specific examples of compounds within this definition are polyols, such as glycerol and pentaerythritol; polyamines, such as tetra amino methane, hexamethylene diamine; and polythiols such as trimercapto ethane; and mixtures such as dihydroxyaminoethane, containing 1 to 30 and preferably 1 to 6 carbon atoms. These precursors may be used in substitution for or in combination with preformed resins. These compounds react with the cyclic nitrile compound to produce a tackfree continuous film of polymer resistant to moisture and shampooing and the normal abrasion encountered in combing the hair.

The reactive hydrogen-containing groups attached to the film-forming resins used in the invention may be unblocked and hence immediately reactive or they may be blocked to prevent the premature reaction of the resin with the cyclic nitrile, in which case they must be deblocked before they can react. The blocking agent is easily removed when the resin is exposed to moisture or heat, depending upon the type of blocking agent employed, very slight amounts of moisture, such as exists in the atmosphere, and very gentle heating being sufficient to deblock the reactive hydrogen functionalities. The determination of whether to use resins containing blocked or unblocked reactive hydrogen-containing groups depends, to a great extent, upon the nature of the hair waving composition and the form in which it is marketed. This will be discussed in more detail below.

The number average molecular weight of suitable film-forming resins varies from about 500 to 500,000 and is preferable in the range of about 1000 to 10,000.

The cyclic nitrile compounds which may be used to prepare the compositions of the invention have the configuration

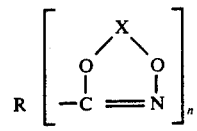

wherein R is an organic radical free of nucleophilic groups and having from 1 to about 200,000 carbon atoms, X is

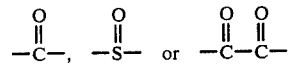

and $n$ is at least 2.

The organic radical designated as R may contain up to about 200,000 carbon atoms; however, it is preferred that the number of carbon atoms in R is 1 to about 10. The organic radical may be monomeric or polymeric and will frequently consist essentially of carbon and hydrogen atoms. By consisting essentially of carbon and hydrogen atoms is meant that the essential composition of the radical is carbon and hydrogen but there can be included therein other elements as well, so long as they do not materially affect the radical's basic characteristic of being non-interfering in the performance of the cyclic nitrile in the waving composition. The R radical may be aromatic, e.g., of 1 to 3 aromatic rings (fused or non-fused) or non-aromatic and, when the latter, can be cyclic or acyclic and saturated or ethylenically or acetylenically unsaturated. Acyclic radicals can be straight or branched chain. The cyclic nitrile groups can be attached to aromatic ring carbon atoms, or to cycloaliphatic ring carbon atoms, or to a non-ring carbon atom. The preparation of the cyclic nitrile compounds used in this invention forms no part of the present invention. The manufacture of these cyclic nitrile adducts is described in detail in U.S. Pats. Nos. 3,531,425 and 3,652,507, 3,702,320, and 3,766,147 which patents are incorporated herein by reference. In the preferred embodiment of the invention, R is a linear or branched chain aliphatic hydrocarbon containing up to 10 carbon atoms.

The group designated above as X may be any one of or combinations of

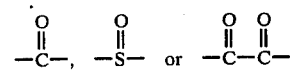

groups. If a catalyst is not used and the curing is conducted at a sufficiently low temperature, the curing step will produce hydroxamates. However, if a catalyst is used or if the curing is conducted at a sufficiently high temperature, the curing will produce urethane linkages with the simultaneous of carbon dioxide from cyclic nitrile groups when X is

sulfur dioxide from cyclic nitrile groups in which X is

and a mixture of carbon dioxide and carbon monoxide when X is

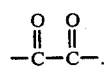

If the composition is to be used in the waving of wigs, or under conditions such that the corresponding hydroxamates would be formed, X may be any one or mixtures of the 3 groups; however, if the composition is to be used for waving the hair of a person, it is preferred that X be

as the use of the other members of the group may produce undesirable or harmful gaseous compounds.

The number of functional groups in the cyclic nitrile compounds, designated above as $n$, is at least 2 and preferably 2 to 4. Compounds in which $n$ is more than 4 may be suitably used in the invention, for example, those prepared by the polymerization of a vinyl cyclic carbonate. However, it is presently preferred that the number of cyclic functional groups be about 2 to about 4.

Illustrative examples of compounds suitable for use in the invention are aliphatic polynitrile compounds such as, malonodi(nitrile sulfide), succinodi(nitrile carbonate), glutarodi(nitrile oxalate), adipodi(nitrile carbonate); aromatic polynitrile compounds such as, benzodi(nitrile sulfide), isophthalodi(nitrile carbonate), and terephthalodi(nitrile oxalate). Examples of the preferred cyclic nitrile compounds are malonodi(nitrile carbonate), succinodi(nitrile carbonate), glutarodi(nitrile carbonate), and adipodi(nitrile carbonate).

The ratio of cyclic nitrile compound to resin may vary from about 0.2 or less to about 2 or more equivalents of cyclic nitrile compound per equivalent of film-forming resin, an equivalent being defined as a cyclic nitrile group in the case of the cyclic nitrile compound and a nucleophilic group in the case of the resin. Although the ratio of cyclic nitrile compound to resin may be less than 0.2 or greater than about 2 equivalents of cyclic nitrile per equivalent of resin, it has been found that the effectiveness of the waving composition begins to diminish as the ratio moves outside of these limits. In the preferred embodiment the equivalent ratio of cyclic nitrile to film-forming resin varies between about 0.8 to about 1.25.

The term flexibilizing adhesion promoter as used in the present discussion is defined as any organic compound which improves the spreadability and wetting properties of the polymeric hair waving composition. In other words, this component of the compositions of the invention serves the dual purpose of providing a more intimate contact between the polymeric waving composition and the hair being waved and improving the flow properties of the polymer so that it spreads more easily and forms a more uniform coating over the individual hair strands. Suitable organic compounds which perform well as flexibilizing adhesion promoters include plasticizers, such as mineral oil, epoxidized soybean oil, and natural and modified castor oils; phthalate esters, such as dioctyl phthalate; waxy polymers, including polyvinyl ethers, such as polyvinyl isobutyl ether, vinyl pyrrolidone polymers such as polyvinylpyrrolidone, quaternized vinylpyrrolidone copolymers, low molecular weight polyamides such as, fatty acid derived polyamides, water-soluble polyamide-epichlorohydrin resins, and alkyd resins, such as oil-modified glycerine-phthalic anhydrine polymer. A useful water-soluble polyamide-epichlorohydrin resin is epichlorohydrin-modified adipic acid-diethylene triamine polymer having an epichlorohydrin to diethylene triamine ratio of 1:1. The quaternized vinylpyrrolidone copolymers contemplated for use in this invention are those of vinyl acetate and compounds having the structural formula:

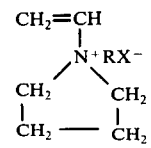

wherein R is an alkyl or aryl radical having up to 8 carbon atoms and X is a halogen ion, particularly chloro or bromo or the hydroxide anion. The mole ratio of vinyl acetate to quaternized vinyl pyrrolidone is about 1:100 to 100:1 and preferably 1:10 to 10:1. Typical vinyl acetatequaternized vinylpyrrolidone copolymers include those of vinyl acetate and 1-ethyl-2-oxo-1-vinyl-pyrrolidinium chloride, 1-phenyl-2-oxo-1-vinylpyrrolidinium bromide, 1-propyl-2-oxo-1-vinylpyrrolidinium hydroxide, 1-vinyl-2-oxopyrrolidinium hydrochloride, etc. The number average molecular weight of suitable polymeric flexibilizing adhesion promoters is about 500 to 500,000 and preferably about 1000 to 10,000. The preferred flexibilizing adhesion promoters are the water-soluble polyamide-epichlorohydrin resins and quaternized vinyl pyrrolidone copolymers.

The amount of flexibilizing adhesion promoter used in the compositions of the invention is any amount effective to produce the desired result, i.e., to improve the spreadability and adhesion properties of the hair waving composition. In general, this amount may vary from about 0.001% to about 50% and preferably about 0.5 to about 20% based on the total weight of solids in the composition. The term solids as used herein means all of the components of the hair waving composition except the solvent used as a vehicle for the basic reactive components of the hair waving composition. Thus, the solids include the organic polymer, the cyclic nitrile compound, the flexibilizing adhesion promoter, the catalyst, if any is used, and any ingredients added to modify the activity of the waving composition and/or the appearance of the hair. As may be appreciated, the lower concentration limit of flexibilizing adhesion promoter in the hair waving composition will vary depending upon the type of polymer, concentration of cyclic nitrile, etc. In some cases trace amounts of flexibilizing adhesion promoter are effective to produce the desired results. The flexibilizing adhesion promoter may be used at concentrations above about 50% of the total weight of solids in the composition but this is not recommended since the permanence characteristics of the finish may begin to diminish.

The rate of reaction of the hair waving composition depends upon the nature of the selected resins and cyclic nitriles and the type and amount of catalyst present, if one is used in the composition. It has been found that amine groups react readily with cyclic nitriles without the presence of a catalyst but hydroxyl and thiol groups react too slowly at room temperature to be very effective without the presence of a catalyst. When the resin contains all or a large number of amine groups, it is not necessary to use a catalyst since the reactivity of the hydrogen atom which is attached to the nitrogen is so great that the reaction between the resin and cyclic amine occurs without the need of a catalyst at room temperature. However, when hydroxyl or thiol groups are present, the reactivity of the hydrogen atoms in these groups is such that the composition must be heated or a catalyst must be used to cause the reaction to proceed at a reasonable rate. Of course, the heat applied in the drying step is usually sufficient to accelerate the reaction between the resin and the cyclic nitrile but it is desirable, though, when using resins containing large amounts of hydroxyl and/or thiol groups to include a catalyst in the hair waving formulation.

Suitable catalysts for the compositions of the invention are those generally found useful to catalyze the reaction between cyclic nitrile and reactive hydrogen-containing compounds. The following catalysts are typical of those which may be used in the compositions of the invention. The catalyst may be a basic material such as, a tertiary amine having a PKa value greater than 3, e.g., triethylamine, as disclosed in U.S. Pat. No. 3,531,425, the disclosure of which is incorporated herein be reference. Another catalyst for use in accordance with the present invention is a combination of a first metal selected from Groups III through V of the Periodic System and a second metal selected from Groups I and III and the iron series of Group VIII of the Periodic Systems as disclosed in U.S. Pat. No. 3,652,507, which disclosure is incorporated herein by reference. Yet another useful catalyst in accordance with the present invention is set forth in U.S. Pat. No. 3,702,320 which disclosure is also incorporated herein be reference. In accordance with this particular application, a compound of aluminum, tin, titanium, zinc, bismuth or ion is dissolved in the reaction mixture. If the compound is one of aluminum, tin, titanium or bismuth, the reaction is run in the absence of metals of Groups I, II, and the iron series of Group VIII of the Periodic System. On the other hand, if the metal compound of zinc or iron, the reaction is run in the absence of metals of Groups III through V of the Periodic System. Other catalysts useful in the present invention are the organic and inorganic fluorides, as disclosed in U.S. Pat. No. 3,766,147 which is incorporated herein by reference. The preferred catalysts are the tertiary aliphatic, aromatic, and heterocyclic tertiary amines such as triethylene diamine, pyridine, N-ethyl morpholine, and N,N-dimethyl aniline. The catalyst, when present, is used at a concentration of about .001 to 10% and preferably about 0.01 to 2.0% based on the total weight of solids in the formulation.

To facilitate the end use of the hair waving composition, the formulation is preferably dissolved in an organic solvent. Any solvent in which the formulation ingredients are soluble can be used in the invention. It is preferred to use volatile solvents which evaporate without leaving a residue. Particularly suitable organic solvents for use in the invention are methylene chloride and the chloro-fluoro alkanes containing up to 3 carbon atoms such as dichlorofluoromethane and dichlorodifluoromethane. Alkanols containing up to 3 carbon atoms, such as methanol, ethanol or isopropanol can be added as a supplement to the solvent to improve the compatability of the solids in the solvent. The concentration of the solids in the solvent depends upon the method of application of the hair waving solution. It is used at a higher concentration when it is to be sprayed on the hair and lower concentration when the hair is to be dipped into the waving solution. Thus, the concentration of solids in the solvent may vary from about 0.5 to about 20% and preferably varies from about 1.0 to 10% based on the total weight of the hair permanent waving solution.

It is preferred to use cosmetically acceptable solvents in the formulations of the invention since the waving solutions can then be used either on the hair of human beings or on wigs, etc. Methylene chloride and the chlorofluoro alkanes are cosmetically acceptable and preferred. The preferred alkanol additive is ethanol.

In addition to the above components, it may be desirable to include in the hair waving formulation a rubbery diene polymer having reactive hydrogen groups such that the polymer may react with the cyclic nitriles and become and integral part of the coating. The advantage of incorporating rubbery polymers into the waving formulation is that they improve the flexibility and shampoo resistance of the coating. Typical of such rubbery polymers are hydroxylated polybutadiene, hydroxylated butadiene-styrene copolymer, hydroxylated butadiene-acrylonitrile copolymer, etc. Suitable reactive hydrogen-containing rubbery diene polymers have a molecular weight of about 600 to 6600 and hydroxyl numbers of about 15 to 180. When reactive hydrogen group-containing rubbery polymers are included in the formulation, they are preferably used at a concentration which provides about 0.001 to 0.5 equivalent per total equivalent of reactive hydrogen-containing compound.

Hair waving products containing the compositions of the present invention may also contain other modifying agents to improve the luster, sheen, body, and softness of the hair being treated as well as agents to improve the attractiveness of the composition such as, perfumes, dyes, and colorants. For example, when lanolin and lanolin derivatives, squalene and squalene derivatives, and white oil or combinations of these are added to the hair waving formulations of the invention, hair treated with the formulation has excellent curl retention. Lanolin and lanolin derivatives found to be effective in improving the curl retention of hair treated according to the invention are anhydrous lanolin, acetylated lanolin, lanolin alcohols, and acetylated lanolin alcohols. The curl retention improving additives are generally most effective at concentrations of up to about 15%, preferably 4 to 10%, based on the total weight of active ingredients.

Products embodying the compositions of the present invention may be of either the single or two package variety. Products sold to professional beauty salons are usually packaged in two container systems since these offer the advantages of lower cost and greater storage stability and the disadvantage of having to mix ingredients presents very little difficulty to professional hairdressers. On the other hand, home users may prefer to use a single container system since the desire for simplicity of applying the hair waving composition outweighs the disadvantage of the higher cost of one package systems.

In two container systems the cyclic nitrile is packaged in one container and the film-forming resin in the other. The various additives may be included in either of the containers since they will not react with either of the major components, i.e., the resin and the cyclic nitrile compound in the absence of the other. It is convenient to combine the resin, which may be reactive, the flexibilizing adhesion promoter, and the catalyst in the selected solvent in one container and the cyclic nitrile and the remaining additives in additional solvent in the second container. With the cyclic nitrile thus isolated from the resin and catalyst, there is no danger of premature reaction occurring. To use the hair waving composition, measured quantities of the two solutions are simply mixed prior to application to the hair.

In one container systems all of the ingredients, including the resin and the cyclic nitrile, are combined in a suitable solvent in one container. To prevent reaction between the resin and the cyclic nitrile from occurring, the reactive hydrogens in the resin are blocked by a suitable blocking agent. As explained above, the resin is prevented from reacting with the cyclic nitrile while the reactive hydrogen is so blocked. Thus, the potentially reactive ingredients may be mixed without reaction. In using these hair waving compositions, they are simply removed from the container and applied to the hair. The particular blocking agents used to render the resin temporarily inactive are a matter of choice and form no part of this invention. Resins containing blocked reactive hydrogen atoms are available commercially and those having the desired properties can be easily selected by those skilled in the art.

In a modification of the two container system, a single container containing a separate compartments can be used to hold and dispense the hair waving composition. In this embodiment, the resin solution is placed in one of the compartments and the cyclic nitrile solution in the other. In this type of system, the two solutions are conveniently stored under pressure and the two solutions are dispensed simultaneously through a three way valve which meters and dispenses the two solutions in the proper ratio. The valve is positioned such that the two streams combine outside of the valving system so that the valve and nozzle will not become clogged due to the reaction of the resin and cyclic nitrile therein. In this system, there is no need to use a resin containing blocked hydrogen functionalities.

It is preferred that the compositions of the invention be substantially anhydrous since water will react slowly with cyclic nitriles to produce hydroxamic acids. When this occurs, the efficiency of the hair waving solution is reduced. It is especially important that the single container products be maintained moisture free if the blocked resin is the type that is deblocked by moisture.

To wave hair by the process of the invention, it is only necessary to apply the compositions disclosed herein to the hair, shape the hair, as by putting it up in curlers, and cure the resinous coating on the hair. Although the compositions of the invention perform satisfactorily on wet or damp hair, it is preferred that the hair be substantially dry when the waving solution is applied; accordingly, if the hair is washed prior to waving, it is preferably dried prior to applying the waving solution.

The order in which the first two steps of the waving process are carried out is not critical. Thus, the hair may be contacted with the waving solution and then shaped or it may be first shaped and then treated with the waving solution. If shaping is to be accomplished by means of curlers, it is usually preferred to mount the hair on the curlers prior to contacting it with the waving solution as this will enable the user to avoid the necessity of handling the hair while it is coated with wet waving solution. On the other hand, if the hair is to be set straight, that is in long straight strands so as to be free of curls or waving, it is usually preferred to apply the permanent waving solution to the hair prior to shaping it. Shaping, in the latter sense, may consist simply in permitting the hair to hang freely of its own weight to produce the long straight hair often considered stylish.

The curing step is carried out after the hair is treated with the waving solution and set in the desired shape. The term curing as used in the present sense means the hardening of the resin to a tough durable film by substantially complete reaction between the resin and the cyclic nitrile.

As the temperature at which the curing is carried out increases, the total time required to effect substantially complete curing diminishes. For example, at room temperature 6 to 8 hours are required to substantially cure the resin, at 100° F. the curing time is 4 hours, at 130° F. the curing time is 2 hours, at 135° F. the curing time is 1 hour, at 140° F. the curing time is ¾ hour, and at 160° F. the curing time is ½ hour. It is preferable to cure the resin coating the hair at the highest tmperature at which the person whose hair is being waved will be comfortable. This will usually be in the neighborhood of 120° to 145° F. Alternatively, the curing can be effected at room temperature over night. It is preferred that the curlers be kept in the hair until the resin is completely cured. However, this is not absolutely necessary and the curlers may be removed after the solvent has been substantially evaporated. In general, the longer the curlers are left in the hair, the tighter will be the resulting permanent wave.

If the curing is carried out at elevated temperatures or with the aid of a catalyst, urethane, urea or thiourethane groups will be formed in the resinous film. As noted previously, this is accompanied by the release of carbon dioxide, sulfur dioxide or mixtures of carbon dioxide and carbon monoxide depending which cyclic nitrile compounds are used in the compositions of the invention. For this reason, the use of cyclic nitrile carbonates is preferred since this results in the release of harmless and odorless carbon dioxide. If the curing is carried out at room temperature in the absence of a catalyst, hydroxamate groups are formed. Since the formation of these groups does not result in the release or the very slow release of the above gases, any of the cyclic nitrile compounds can be freely used in compositions used at room temperature without a catalyst. Depending on the cure temperature used, there may be a mixture of both hydroxamate and urethane, urea or thiourethane groups present in the finished coating. However, it is preferred to react the compositions of the invention under conditions such that urethane, urea or thiourethane linkages are formed in the resin, hence the preference for cyclic nitrile carbonates.

The method of applying the hair waving solution to the hair is a matter of choice. It is often convenient to apply the hair waving solution by means of an aerosol spray. However, when the waving solution is applied in this method, care must be taken to insure that all of the hair is thoroughly wetted with the waving solution. The waving solution may also be applied by means of a squeeze bottle having a small opening so that the amount of lotion can be easily controlled. Either of the above methods for applying the waving lotion to the hair may be employed regardless of whether the hair is to be mounted on curlers prior to or subsequently to applying the waving solution. If it is desired to wave only the ends of the hair, these may be mounted on curlers and dipped into a container such as a small dish of waving solution. If it is desired to remove the natural curl from the hair, that is to use the hair waving solution to straighten the strands of hair, this can be accomplished by combing the hair and letting it hang straight until the cure is completed as described above.

The present invention provides users with a number of advantages. When the hair waving solution is applied and properly cured, a strong continuous film will be developed over the entire surface of the hair strand. This film will be tightly adherent to the hair and will resist removal by combing or by repeated shampoos and subsequent combing. Hair which has been waved and set according to this invention possesses exceptionally high curl retention and bounce back even when it is subjected to prolonged exposure to very high humidity. The term bounce back is used to describe the ability of hair to recover curl after it has been shampooed, dried, and combed. As is evident from the above disclosure, the hair waving process of the present invention is very much shorter than the conventional permanent waving procedures. The composition used in the present invention causes no damage to the hair or scalp whereas the conventional hair waving compositions are often harsh and may cause permanent damage to the hair or scalp.

The following examples illustrate specific embodiments of the invention. Unless otherwise indicated, parts and percentages are on a weight basis.

EXAMPLE I

A

Hair swatches were prepared by the following procedure: Several 3 gram samples of human hair, previously shampooed and dried, are adhesively bound at one end to cardboard supports to produce hair swatches about 1½ wide and 7½ long. The swatches were allowed to age three days at laboratory conditions to come to constant weight. Prior to contact with the hair waving solution the swatches were rolled and fastened onto ¾ diameter plastic rollers.

B

A 2% by weight solution of an acrylic copolymer consisting of 80 mole % n-butyl acrylate and 20 mole % of di-n-butyl ketimino ethyl acrylate having a number average molecular weight of 6000 and ADNC (adipodinitrile carbonate) in an equivalent ratio of acrylic copolymer to ADNC of 1:1 is made up using methylene chloride as the solvent. To this, 2%, based on the weight of the total solution of a copolymer consisting of 80 mole % vinyl acetate and 20 mole % of 1-ethyl-2-oxo-1-vinylpyrrolidinium chloride having a number average molecular weight of 2000 and 1% based on the total weight of solids of triethylene diamine catalyst is added. Some of the hair swatches prepared above are dipped into a beaker containing the hair waving solution for 2 minutes, after which they are removed and allowed to drain free of solution. The swatches, still mounted on the plastic rollers, are then dried in a forced-draft oven set at 140° F for 45 minutes. The hair swatches are then carefully removed from the curlers.

After the swatches of Example IB are exposed to an atmosphere on 94% relative humidity at a temperature of 100° F for 24 hours or are dry-combed 5 to 10 strokes with a coarse comb or shampooed twice with a 1% aqueous solution of a commercial hair shampoo at 120° F and dried are combed 5 to 10 strokes they will retain at least 90% of their initial curl.

EXAMPLE II

Hair swatches prepared as in Example IA are contacted with a 0.4% aqueous solution of a modified polyamide having a final number average molecular weight of 1500 prepared by reacting an adipic acid-diethylenetriamine polyamide with epichlorohydrin at a secondary amine: epichlorohydrin ratio of 1:1. The hair swatches are then treated with a mixture comprised of 1% triethylene diamine based on the weight of the butyl acrylate copolymer and adipodinitrile carbonate and a 2% by weight methylene chloride solution of the acrylic copolymer used in Example IB and adipodinitrile carbonate in an equivalent ratio of acrylic copolymer to adipodinitrile carbonate of 1:1. The hair swatches are then curled.

After the swatches are exposed to an atmosphere of 94% relative humidity at a temperature of 100° F for 24 hours or dry combed 5 to 10 strokes with a coarse comb or shampooed twice with a 1% aqueous solution of a commercial hair shampoo at 120° F and dried and combed 5 to 10 strokes they will retain at least 90% of their initial curl.

EXAMPLE III

Hair swatches are prepared and waved in accordance with the procedure of Example I except that 4%, based on the weight of the total mixture, of white mineral oil is substituted for the vinyl acetate-quaternized vinylpyrrolidone copolymer. After the resulting hair swatches are subjected to any one of the tests set forth in Example IB they will retain about 75 to 89% of their initial curl.

EXAMPLE IV

Hair swatches are prepared and waved in accordance with the procedure of Example I except that the catalyst was omitted from the waving formulation. After the resulting hair swatches are subjected to any one of the tests set forth in Example IB they will retain about 75 to 89% of their initial curl.

EXAMPLE V

Hair swatches are prepared and waved in accordance with the procedure of Example I except that 0.1% based on the total weight of solids of an adipic acid-diethylenetriamine polyamide modified by reaction with epichlorohydrin at a secondary amine to epichlorohydrin ratio of 1:1 and having a final number average molecular weight of 2500 is substituted for the quaternized vinylpyrrolidone vinyl acetate copolymer. After the resulting hair swatches are subjected to any one of the tests set forth in Example IB they will retain about 75 to 89% of their initial curl.

EXAMPLE VI

Hair swatches are treated as in Example I except that 20% based on equivalents of the butyl acrylate copolymer is replaced by hydroxylated butadiene-styrene copolymer containing 75 mole % butadiene and 25 mole % styrene and having a number average molecular weight of 3200. The treated hair swatches will have the same fine properties noted in Example I hair swatches and they will be capable of being dry combed severely and shampooed without significant loss of curl level.

EXAMPLE VII

Hair swatches are treated as in Example I except that 10% based on the weight of ADNC and butyl acrylate copolymer of a mixture containing 4 parts of acetylated lanolin and 1 part of squalene is added to the formulation. The treated hair swatches will have the same fine properties noted in Example I hair swatches and improved curl retention.

COMPARATIVE EXAMPLE A

Hair swatches are treated as in Example I except that the vinyl acetate-quaternized vinyl pyrrolidone copolymer is omitted from the formulation. The resulting hair swatches are subjected to any one of the tests set forth in Example IB. They will retain little or none of their initial curl.

Examples I through VII illustrate various embodiments of the invention. Comparative Example A illustrates the necessity of including the flexibilizing adhesion promoter in the formulations of the invention.

Although the invention has been described with particular reference to specific examples, it is contemplated that modifications of these may be employed, for example, the hair may be dried at room temperature. Also, although detached human hair is treated in the Examples, it is intended to include in the invention the treatment of the hair attached to human beings as well as natural or synthetic fibers which contain the linkages necessary to obtain the desired results of the invention. Accordingly, the breadth of the invention is limited solely by the scope of the appended claims.

We claim:

1. A composition useful for waving hair comprising
   a. at least one hydroxyl, amine, or thiol group-containing acrylic or methacrylic film-forming resin having a number average molecular weight of about 500 to 500,000 or polyol, polyamine or polythiol resin forming precursor containing 1 to 30 carbon atoms,
   b. a cyclic nitrile compound of the formula:

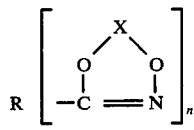

wherein R is an organic radical free of nucleophilic groups and having 1 to about 200,000 carbon atoms, X is a member selected from the group consisting of

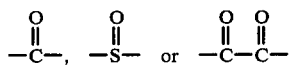

and $n$ is at least 2, and
   c. a flexibilizing adhesion promoter.

2. The composition of claim 1 including a catalyst which catalyzes the reaction between (a) and (b).

3. The composition of claim 2 wherein said catalyst is a tertiary amine and it is present in an amount of about 0.01 to about 2.0% based on the total weight solids present.

4. The composition of claim 1 wherein X is

and $n$ is about 2 to 4 and the equivalent ratio of cyclic nitrile to resin is about 0.8 to 1.25.

5. The composition of claim 4 wherein R is an organic radical having 1 to about 10 carbon atoms.

6. The composition of claim 1 wherein said flexibilizing adhesion promoter is a member selected from the class consisting of plasticizers, quaternary vinyl pyrrolidone polymers, and the product of the reaction between water-soluble polyamides containing secondary amine groups and epichlorohydrin and it is present in an amount effective to produce the desired result up to about 50% based on the total weight of solids.

7. The composition of claim 6 wherein the flexibilizing adhesion promoter is a vinyl acetate-quaternary vinyl pyrrolidone copolymer.

8. The composition of claim 6 wherein said flexibilizing adhesion promoter is the product of the reaction between water-soluble polyamides containing a secondary amine group and epichlorohydrin.

9. A hair waving solution comprises of about 0.5 to about 20% or the composition of claim 1 and about 99.5 to about 80% of an organic solvent in which said composition is substantially soluble.

10. A hair waving solution comprises of about 1 to about 10% of the composition of claim 2 and about 99 to about 90% of an organic solvent in which said composition is substantially soluble.

11. A hair waving solution comprises of about 1 to about 10% of the composition of claim 6 and about 99 to about 90% of an organic solvent in which said composition is substantially soluble.

12. The hair waving solution of claim 10 wherein said catalyst is a tertiary amine and it is present in an amount of about 0.01 to about 2.0%, based on the total weight of solids.

13. The hair waving solution of claim 11 wherein said organic solvent is selected from the group consisting of methylene chloride and chlorofluoro alkanes containing up to 3 carbon atoms and mixtures of these, said percentages being based on the total weiht of said composition and solvent.

14. The hair waving solution of claim 13 wherein

and $n$ is about 2 to 4.

15. The hair waving solution of claim 14 wherein R is a hydrocarbon radical containing 1 to 10 carbon atoms.

16. The hair waving solution of claim 10 wherein said flexibilizing adhesion promoter is a quaternary vinyl pyrrolidone polymer.

17. The hair waving solution of claim 10 wherein said flexibilizing adhesion promoter is the product of the reaction between water-soluble polyamides containing a secondary amine group and epichlorohydrin.

18. The hair waving solution of claim 10 containing, as a supplement to said solvent, an alkanol containing up to 3 carbon atoms.

19. The hair waving solution of claim 18 wherein said alkanol is ethanol.

20. A composition useful for waving hair comprising
   a. a film-forming polyacrylate having pendant groups which contain reactive hydrogens,
   b. a cyclic nitrile carbonate of the formula

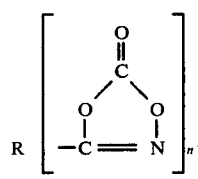

wherein R is an organic radical free of nucleophilic groups and having 1 to 10 carbon atoms, and n is 2 to 4, c. a flexibilizing adhesion promoter selected from the class consisting of quaternary vinyl pyrrolidone and water-soluble polyamides containing secondary amine groups and epichlorohydrin, and d. a catalyst.

21. The composition of claim 20 wherein said catalyst is tertiary amine and it is present in an amount of about 0.01 to about 2.0%, based on the total weight of the solids present.

22. The composition of claim 21 wherein said cyclic nitrile carbonate is adipodi(nitrile carbonate).

23. A hair waving solution comprised of 3 to 6% of the composition of claim 21 and 97 to 94% of an organic solvent selected from the class consisting of methylene chloride, chlorofluoro alkanes containing up to 2 carbon atoms, and mixtures of these.

24. The hair waving solution of claim 23 additionally containing an alkanol containing up to 2 carbon atoms.

25. A method for waving hair comprising contacting said hair with the composition of claim 1, shaping the hair, and drying said hair.

26. A method for waving hair comprising contacting said hair with the composition of claim 2, shampooing the hair, and drying said hair.

27. The method of claim 25 wherein said drying is conducted at a temperature of 70° to 150° F.

28. The method of claim 27 wherein said drying is conducted at a temperature sufficiently high to substantially cure said film-forming resin.

29. A method for imparting a permanent wave to hair comprising treating said hair with the solution of claim 10, shaping the hair, and drying said hair.

30. The method of claim 29 wherein said hair is wound on their curlers prior to treating the hair with said solution.

31. The method of claim 29 wherein said hair is wound on curlers subsequently to treating the hair with said solution.

32. The method of claim 29 wherein said solution is applied to the hair by spraying.

33. The composition of claim 1 wherein up to about 50% on an equivalent basis of the reactive hydrogen film-forming resin or resin-forming precursor is replaced by a reactive hydrogen-containing butadiene polymer having a molecular weight of about 600 to 6600 and a hydroxyl number of about 15 to 180.

34. The composition of claim 1 including up to about 15%, based on the total weight of active ingredients, of an additive selected from the group consisting of lanolin, lanolin derivatives, squalene, and mixtures of these.

* * * * *